(12) United States Patent
Butler et al.

(10) Patent No.: US 8,584,994 B2
(45) Date of Patent: Nov. 19, 2013

(54) FLOOR STAND WITH ANGLED ARM FOR MICROSCOPE

(75) Inventors: Jonathan Michael Butler, Gainsville, GA (US); Robert Troy Hewlett, Cumming, GA (US); Robert Jeffrey Hewlett, Dawsonville, GA (US); Robert McCoy Hewlett, Cumming, GA (US)

(73) Assignee: Endure Medical, Inc., Cumming, GA (US)

( * ) Notice: Subject to any disclaimer, the term of this patent is extended or adjusted under 35 U.S.C. 154(b) by 0 days.

(21) Appl. No.: 13/279,046

(22) Filed: Oct. 21, 2011

(65) Prior Publication Data

US 2013/0099072 A1    Apr. 25, 2013

(51) Int. Cl.
*F16M 11/00*    (2006.01)

(52) U.S. Cl.
USPC ............ 248/162.1; 248/123.11; 248/125.7; 248/125.8; 248/122.1; 248/280.11; 362/401; 359/368

(58) Field of Classification Search
USPC ............ 248/123.11, 125.7, 125.8, 122.1, 248/280.11, 292.11, 162.1, 431, 281.11, 248/123.2; 362/401, 402, 419, 422; 359/382, 384, 368, 381, 419
See application file for complete search history.

(56) References Cited

U.S. PATENT DOCUMENTS

| | | | | |
|---|---|---|---|---|
| 5,213,293 A | * | 5/1993 | Muentener et al. | 248/123.11 |
| 6,050,530 A | * | 4/2000 | Nakamura | 248/123.2 |
| 6,098,936 A | * | 8/2000 | Birrell | 248/122.1 |
| 6,254,046 B1 | * | 7/2001 | Biber | 248/287.1 |
| 6,471,165 B2 | * | 10/2002 | Twisselmann | 248/123.11 |
| 6,592,086 B1 | * | 7/2003 | Sander | 248/123.11 |
| 6,899,307 B2 | * | 5/2005 | Strauss et al. | 248/280.11 |
| 7,461,824 B2 | * | 12/2008 | Poxleitner et al. | 248/278.1 |
| 8,038,108 B2 | * | 10/2011 | Yasunaga et al. | 248/123.2 |
| 8,132,769 B2 | * | 3/2012 | Metelski | 248/281.11 |
| 2004/0190131 A1 | * | 9/2004 | Brenner et al. | 359/384 |

* cited by examiner

*Primary Examiner* — Terrell McKinnon
*Assistant Examiner* — Michael McDuffie
(74) *Attorney, Agent, or Firm* — Keiko Ichiye

(57) ABSTRACT

A floor stand with an angled arm is provided for use with a microscope. The angled arm allows the floor stand and microscope to fit within a small or crowded examination room while also allowing a physician and his assistant space to maneuver around the floor stand and examine a patient.

9 Claims, 2 Drawing Sheets

FLOOR STAND WITH ANGLED ARM FOR MICROSCOPE

FIELD OF THE INVENTION

The invention relates generally to stands for medical devices.

BACKGROUND ART

The background art in floor stands for surgical microscopes provides little space for physicians and their assistants to maneuver around the stand or the medical device. This invention supplies a need for a surgical microscope floor stand that can unobtrusively fit within a small or crowded room while simultaneously providing the physician or other personnel additional space around the microscope and patient for ease of positioning or maneuvering.

SUMMARY OF THE INVENTION

In some aspects, the invention relates to a floor stand with an angled arm for a microscope having a base comprising means for moving about the floor connected to a central pillar, a support column having a top end, a bottom end, and a column longitudinal axis, the bottom end being connected to the top of the central pillar, and the top end connected to a first end of a lateral arm and the top end extending downward from the first end of the lateral arm, the lateral aim having a first end, a second end, and an arm longitudinal axis substantially parallel to the floor, such that the column longitudinal axis intersects the arm longitudinal axis at an angle between 50 and 70 degrees, inclusive, and an articulating arm having a pivot end and an attachment point end, the pivot end being connected to the second end of the lateral arm, and the attachment point end having means to attach a microscope.

In other aspects, the invention relates to a floor stand wherein the lateral arm and the support column are of a unitary construction.

In other aspects, the invention relates to a floor stand wherein the support column is straight.

In other aspects, the invention relates to a floor stand wherein the lateral arm is straight.

In other aspects, the invention relates to a floor stand wherein the support column has a plurality of sections, where each section is straight and the support column bends at the junction of each section.

In other aspects, the invention relates to a floor stand wherein the articulating arm is pivotally connected to the lateral arm, such that the articulating arm is capable of moving vertically and horizontally.

Other aspects and advantages of the invention will be apparent from the following description and the appended claims.

BRIEF DESCRIPTION OF DRAWINGS

It should be noted that identical features in different drawings are shown with the same reference numeral.

DETAILED DESCRIPTION

Figure 1:
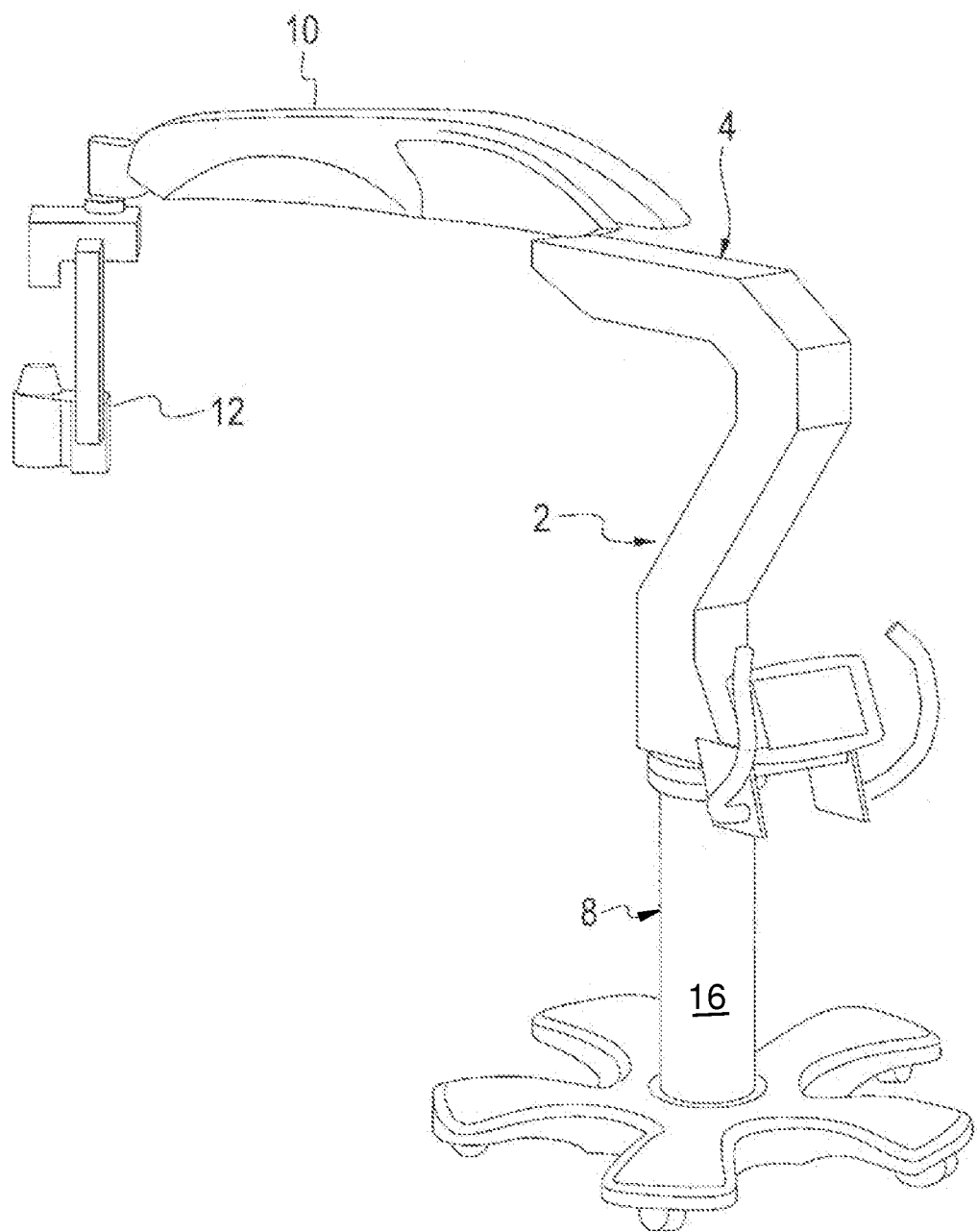
FIG. 1 depicts a perspective view of one embodiment of the invention.
Figure 2:
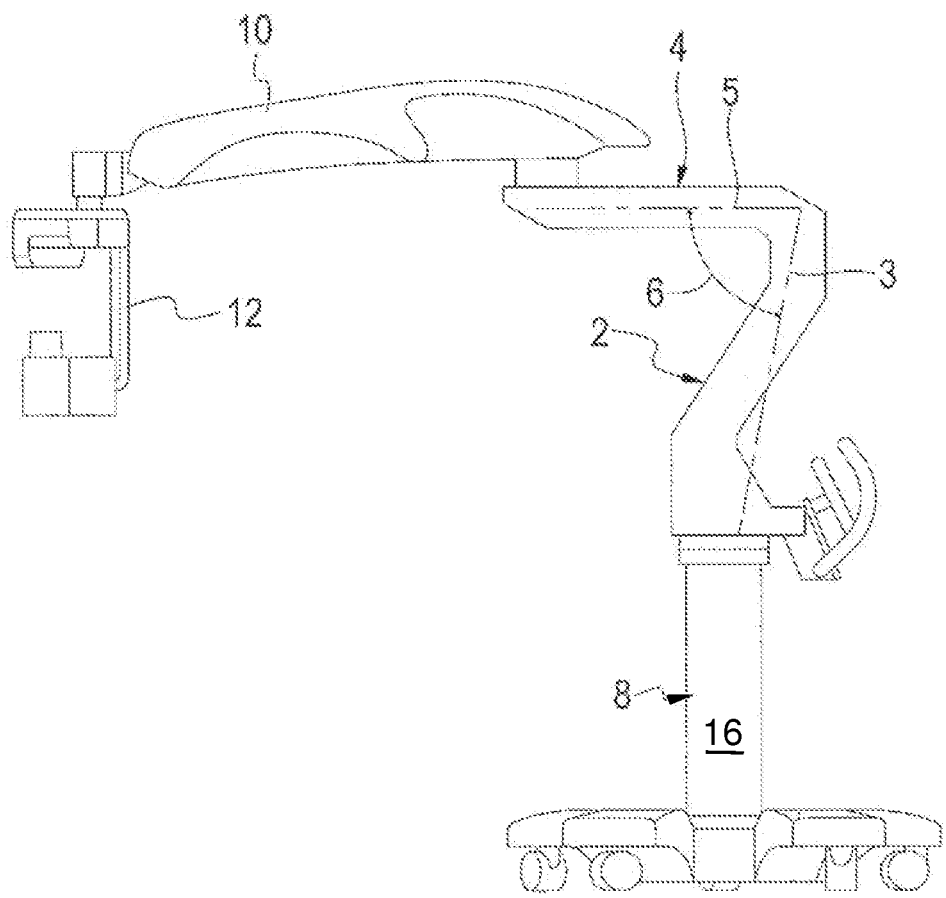
FIG. 2 depicts a side elevational view of one embodiment of the invention and the arm longitudinal axis and the column longitudinal axis for the given embodiment, with the angle formed by their intersection.

The invention is a floor stand designed to allow doctors and their assistants ease of access to a patient while using a surgical microscope for surgery or examination attached to the floor stand. In one embodiment of the invention, a support column 2 rises diagonally from a base 8 to support a lateral arm 4. The base 8 has wheels, castors, or any method for being moved about the floor. The base 8 also has a central pillar 16 which is vertical, at the top of which the support column 2 is rigidly mounted. The support column 2 may rise diagonally from the base 8 straight without bends or curves. Alternatively, the support column 2 may be bent into multiple longitudinal sections or be curved, but this is considered the same invention so long as the support column 2 as a whole has a column longitudinal axis 3 that intersects the arm longitudinal axis 5 at an angle 6 in the range of about 50 to 70 degrees, inclusive. The column longitudinal axis 3 is defined as the axis that includes the line segment running from the middle of the bottom end of the support column 2 to the support column's 2 center of mass. The center of mass is calculated according to the standard formula for determining the center of mass of a physical object: $CM(x,y,z)=\Sigma(m_i*r(x,y,z)_i)*(1/M)$, where $CM(x,y,z)$ is the position of the center of mass in a three-dimensional Cartesian space, $m_i$, is a given individual mass element, $r(x,y,z)$; is the position of the given individual mass element in the three-dimensional Cartesian space, and M is the total mass of all the individual mass elements in the system. For a continuous system, this becomes the integral equation $CM(x,y,z)=(1/M)*(\int p(r)*r(x,y,z)*dV)$, where $CM(x,y,z)$ is the position of the center of mass in a three-dimensional Cartesian space, M is the total mass of the body, $r(x,y,z)$ is the position of a differential mass element of the body in the three-dimensional Cartesian space, $p(r)$ is the density of the object at the given position $r(x,y,z)$, and dV is the differential of volume. The intersection of the arm longitudinal axis 5 and the column longitudinal axis 3 can be at a location inside or outside of the lateral arm 4 or the support column 2. For example, a support column 2 in the shape of a "C" that is connected to the bottom end of the "C" to the central pillar 16 of the base 8 and at the top end of the "C" to the lateral arm 2 would have a column longitudinal axis 3 that extends beyond the upper left section of the "C"-shaped support column 2.

In one embodiment the lateral arm 4 is rigidly mounted at its first end to the top end of the support column 2 and its second end is connected to an articulating arm 10. The lateral arm 4 has an arm longitudinal axis 5 that is substantially parallel to the ground. The arm longitudinal axis 5 is defined as the axis through the lateral arm's 4 center of mass about which the lateral arm 4 would rotate freely due to a twisting force on the lateral arm 4. The lateral arm 4 may be substantially straight. Alternatively, the lateral arm 4 may be bent into multiple longitudinal sections or be curved. In these embodiments, the lateral arm 4 is defined as the section of the structure that has an arm longitudinal axis 5 that is substantially parallel to the ground. The intersection of the column longitudinal axis 3 and the arm longitudinal axis 5 results in an angle in the range of about 50 to 70 degrees, inclusive. The angle 6 is defined as having one side as the arm longitudinal axis 5, the second side as the column longitudinal axis 3, and the vertex as the intersection point of the two axes. The angle 6 allows for an. open space between the lateral arm 4 and the support column 2 such that the stand can fit within a tight or enclosed space, such as next to a patient's chair or table, while simultaneously providing the physician or other personnel additional room to maneuver or position themselves while examining the patient.

In one embodiment, the support column 2 and the lateral arm 4 are two separate structures rigidly mounted together. Alternatively, in another embodiment the support column 2 and the lateral arm 4 are of a unitary construction or mold. If the support column 2 and the lateral arm 4 are a unitary structure, the lateral arm 4 can be defined in one embodiment as the upper, lateral portion of the unitary structure that, if separate from the rest of the structure, would have an arm longitudinal axis 5 as defined above that is substantially parallel to the ground. The support column 2 is defined as the remainder of the unitary structure. The column longitudinal axis 3 is then defined as the axis including the line segment running from the middle of the bottom end of the support column 2 through the center of mass of the section of the unitary structure defined as the support column 2.

In another embodiment of the invention, the support column 2 and lateral arm 4 combine to form a single middle support member having a lower end and an upper end. The lower end is rigidly mounted to the pillar 16 of the base 8, and the upper end is connected to the articulating arm 10. The middle support member comprises an upper section and a lower section. The upper section is defined as extending from the upper end to the point of the middle support member furthest removed from the upper end along an axis parallel to the ground. The arm longitudinal axis 5 is defined in this embodiment as the axis passing through the upper section's center of mass that is substantially parallel to the ground. The lower section of the middle support member is defined as the remainder of the middle support member. The column longitudinal axis 3 is defined in this embodiment as the axis that includes the line segment beginning at the middle of the lower end of the middle support member and ending at the center of mass of the lower section. The angle 6 formed by the intersection of the column longitudinal axis 3 and the arm longitudinal axis 5 is in the range of about 50 to 70 degrees, inclusive.

In one embodiment, an articulating arm 10 connects to the free or second end of the lateral arm 4 to provide additional space for maneuverability and to allow the physician to grossly position the microscope 12 for use with a patient. The articulating arm 10 may be fixed to the second end of the lateral arm 4, or it may be pivotally connected to the lateral arm 4, such that the articulating arm 10 is capable of moving vertically and horizontally. The microscope 12 is attached to the device end of the articulating arm 10.

Alternatively, the microscope 12 may be attached directly to the second end of the lateral arm 4.

While the invention has been described with respect to a limited number of embodiments, those skilled in the art, having benefit of this disclosure, will appreciate that other embodiments can be devised which do not depart from the scope of the invention as disclosed here. Accordingly, the scope of the invention should be limited only by the attached claims.

What is claimed is:

1. A floor stand with an angled arm for a microscope comprising: a base comprising means for moving about the floor, the base being coupled to a central pillar, a support column having a top end, a bottom end, and a column longitudinal axis, the bottom end being coupled to the top of the central pillar, the top end connected to a first end of a lateral arm and the top end extending downward from the first end of the lateral arm, the support column having a C-shape that is connected at the bottom end of the C-shape to the central pillar of the base and at the top end of the C-shape to the lateral arm, the lateral arm having the first end, a second end, and an arm longitudinal axis substantially parallel to the floor, such that the column longitudinal axis intersects the arm longitudinal axis at an angle between about 50 and 70 degrees, inclusive, the support column being at least as long as the lateral arm and bent into at least two longitudinal sections; and an articulating arm having a pivot end and an attachment point end, the pivot end being connected to the second end of the lateral arm, and the attachment point end having means to attach a microscope.

2. The floor stand of claim 1 wherein the lateral arm and the support column are of a unitary construction.

3. The floor stand of claim 1 wherein the support column is straight.

4. The floor stand of claim 1, wherein the lateral arm is straight.

5. The floor stand of claim 1, further comprising the support column having a plurality of sections and the support column bends at the junction of each longitudinal section.

6. The floor stand of claim 1 further comprising the articulating arm being pivotally connected to the second end of the lateral arm, such that the articulating arm is capable of moving vertically and horizontally.

7. The floor stand of claim 1 wherein the support column is at least partially curved.

8. The floor stand of claim 1 wherein the lateral arm is at least partially curved.

9. A floor stand with an angled arm for a microscope comprising: a base comprising means for moving about the floor, the base being coupled to a central pillar, a middle support member having a C-shape comprising a lower end and an upper end, said lower end connected to the central pillar and said upper end coupled to an articulating arm, wherein the middle support member comprises: an upper section having an arm longitudinal axis passing through the upper section's center of mass and substantially parallel to the ground, a lower section having a column longitudinal axis including a line segment commencing at the middle of the lower end and continuing to the center of mass of the lower portion, the lower section being at least as long as the upper section, said arm longitudinal axis intersecting said column longitudinal axis at an angle between about 50 and 70 degrees, inclusive, the lower section bent into at least two longitudinal sections, and the articulating arm having a pivot end and an attachment point end, the pivot end being connected to the upper end of the middle support member, and the attachment end having means to attach to a microscope.

* * * * *